US007680609B2

(12) United States Patent
Natsume et al.

(10) Patent No.: US 7,680,609 B2
(45) Date of Patent: Mar. 16, 2010

(54) BIOPOLYMER AUTOMATIC IDENTIFYING METHOD

(75) Inventors: Tohru Natsume, Tokyo (JP); Hiroshi Nakayama, Tokyo (JP)

(73) Assignee: National Institute of Advanced Industrial Science & Technology, Tokyo (JP)

( * ) Notice: Subject to any disclaimer, the term of this patent is extended or adjusted under 35 U.S.C. 154(b) by 973 days.

(21) Appl. No.: 10/526,464

(22) PCT Filed: Sep. 4, 2003

(86) PCT No.: PCT/JP03/11298

§ 371 (c)(1), (2), (4) Date: Aug. 15, 2005

(87) PCT Pub. No.: WO2004/023132

PCT Pub. Date: Mar. 18, 2004

(65) Prior Publication Data

US 2006/0100792 A1 May 11, 2006

(30) Foreign Application Priority Data

Sep. 5, 2002 (JP) ............................ 2002-259737

(51) Int. Cl.
*G01N 27/62* (2006.01)
*G01N 27/70* (2006.01)
*H01J 49/26* (2006.01)
*G01N 33/483* (2006.01)

(52) U.S. Cl. ............................ 702/27; 702/19; 436/89; 436/94; 436/173; 530/350

(58) Field of Classification Search .................... 702/19
See application file for complete search history.

(56) References Cited

U.S. PATENT DOCUMENTS

2002/0102610 A1 8/2002 Townsend et al.

FOREIGN PATENT DOCUMENTS

JP 10-132786 A 5/1998

OTHER PUBLICATIONS

Volker Egelhofer et al., "Protein Identification by MALDI-TOF-MS Peptide Mapping: A New Strategy", Analytical Chemistry, vol. 74, Apr. 2002, pp. 1760-1771.

E. Mortz et al., "Identification of Proteins in Polyacrylamide Gels by Mass Spectrometric Peptide Mapping Combined with Database Search", Biological Mass Spectrometry, vol. 23, May 1, 1994k, p-p. 249-261.

J. Gobom et al., "A Calibration Method That Simplifies and Improves Accurate Determination of Peptide Molecular Masses by MALDI-TOF-MS", Analytical Chemistry, vol. 74, Aug. 1, 2002, pp. 3915-3923.

International Search Report of PCT/JP03/11298, Dec. 2003.

V. Egelhofer et al., "Improvements in Protein Identification by MALDI-TOF-MS Peptide Mapping", Analytical Chemistry, Jul. 1, 2000, vol. 72, No. 13, pp. 2741 to 2750.

*Primary Examiner*—Michael Borin
(74) *Attorney, Agent, or Firm*—Stephen A. Bent; Foley & Lardner LLP

(57) ABSTRACT

The invention aims to provide a highly accurate automatic biopolymer determination technique utilizing mass spectrometry whereby calibration prior to measurement or the addition of an internal standard to a sample can be eliminated. The biopolymer automatic identifying method of the invention comprises: retrieving a candidate molecule by matching an observed mass value X obtained by mass spectrometry with a predetermined database; selecting an arbitrary number of candidate molecules with high similarity scores; calibrating the observed mass value X using the candidate molecule as an internal standard; calculating relative error Ec between a calibrated mass value Xc and a theoretical mass value M of the candidate molecule; determining the standard deviation $S_{Ec}$ of the relative error; determining a tolerance Tc of database search from the standard deviation $S_{Ec}$; and repeating a database search based on the tolerance Tc.

6 Claims, 4 Drawing Sheets

BIOPOLYMER AUTOMATIC IDENTIFYING METHOD

TECHNICAL FIELD

The present invention relates to a biopolymer identifying technology utilizing mass spectrometry, and more specifically, to a biopolymer automatic identifying method capable of improving the accuracy of mass data obtained by mass spectrometry.

BACKGROUND ART

Mass spectrometry is an instrumental analysis technique whereby sample molecules are ionized and then separated in accordance with the mass/charge ratio (m/z) for detection. Using this technique, qualitative analysis can be performed based on the resultant mass spectrum, and quantitative analysis can be performed based on ion quantities.

The mass spectrometer ("MS") used for such a measurement of molecular mass roughly consists of an ionization unit (ion source) for ionizing a sample, an analyzer for separating ions in accordance with the mass/charge ratio m/z (m: mass, and z: charge number), a detection unit (detector) for detecting separated ions, and a data analysis unit.

When subjecting sample molecules to mass spectrometry using the aforementioned mass spectrometer, the mass spectrometer must be calibrated prior to measurement. Specifically, since errors might be introduced into the measurement by the mass spectrometer due to factors such as temperature changes, voltage accuracies, and electric circuit noise, a calibration procedure must be carried out prior to the start of measurement. In the calibration procedure, the chromatograph or the like is removed from the mass spectrometer, and a predetermined mass-calibration standard substance is introduced into the mass spectrometer so as to obtain an observed mass value. The observed mass value is compared with a known theoretical mass value, and the apparatus is adjusted such that no systematic error occurs in mass values (a calibration procedure according to the external standard method).

If an even higher accuracy of mass values is to be obtained, an additional calibration procedure must be performed, whereby a known substance is mixed in the sample and its mass is measured, and the actual measurement value is adjusted based on the mass value (a calibration procedure according to the internal standard method).

In general, identification of biopolymers, such as peptides or proteins, using a mass spectrometer (including the tandem mass spectrometer) involves a procedure referred to as a database search (or a library search). In this procedure, the observed mass value of an unknown sample molecule obtained by mass spectrometry is searched for by matching with a database (library) in which the primary structures or sequences of approximately 100,000 kinds of molecules are stored. In an expected reference (standard) spectrum calculated based on the structure information, molecules with a spectrum similar to that of the unknown molecule under investigation are allocated scores and selected. Candidate molecules are thus narrowed and listed, thereby eventually identifying the unknown sample molecule.

However, the above-described mass spectrometer calibration procedure is very troublesome work, requires much adjustment time, and is primarily responsible for the drop in work efficiency caused by the conventional mass measurement operation. Namely, it has been impossible to carry out a measurement operation with high efficiency based on a continuous operation of the mass spectrometer (without calibration). Further, in a measurement system employing a plurality of mass spectrometers, it has been extremely difficult to achieve uniform accuracy and reliability in the individual apparatuses even if they are calibrated individually according to the external standard.

In the case of the external standard calibration, it has been impossible, using the conventional process of database search as described above, to eliminate from the measurement data the influence of erroneous measurement in the mass spectrometer produced by influences of the external environment. Particularly, even those measurement errors due to subtle temperature changes (on the order of 0.2° C.) in the measurement environment could not be ignored in some cases.

Furthermore, when a complex biopolymer mixture is measured by the conventional internal standard calibration method, the internal standard substance and the ion signals from the sample are superposed, which prevents ion analysis. Thus, it has been difficult to select the type or concentration of the substance that is put into the sample as the internal standard. In order to achieve high mass accuracy for a wide range of masses, it has been necessary to introduce a number of internal standard substances.

Also, human confirmation of each identification result has been necessary, as the identification reliability has been low. Recent progress in mass spectrometry, however, has made direct analysis of increasingly more complex biopolymer mixtures possible. This has resulted in huge volumes of data that could not possibly be individually confirmed by the human eyes. Therefore, there has been a need to develop a highly reliable automatic identification technique for the analysis of complex biopolymer mixtures.

DISCLOSURE OF THE INVENTION

It is therefore an object of the invention to provide a highly accurate and reliable method for automatically identifying biopolymers that is based solely on data processing and that eliminates the need for calibration of the mass spectrometer prior to measurement or the addition of an internal standard to the sample in advance.

In order to achieve the aforementioned object, the invention provides a biopolymer automatic identifying method implementing the following procedures (1)-(7):

(1) A mass measurement procedure for measuring the mass of a biopolymer in a sample by mass spectrometry; (2) A database search procedure for searching a predetermined database for candidate molecules by matching an observed mass value obtained by said mass measurement procedure with the predetermined database; (3) a candidate molecule selection procedure for selecting an arbitrary number of candidate molecules having a high similarity score; (4) a mass value calibration procedure for calibrating the observed mass value using the candidate molecules as an internal reference; (5) a procedure for calculating relative error between a calibrated mass value of a candidate molecule obtained in a previous procedure and a theoretical mass value in order to determine the standard deviation of such relative error; (6) a procedure for determining the tolerance (allowable error) of the database search procedure based on the standard deviation; and (7) a procedure for repeating the database search procedure on the basis of the tolerance. The term "database" herein refers to a database of molecular structures or sequences.

The mass value calibration procedure (4) may be a procedure in which relative error between an actual measurement value and a theoretical mass value of a candidate molecule selected by the candidate molecule selection procedure is calculated and a systematic error in the observed mass value is estimated by creating a least square line (a line expressed by the equation y=a×M+b, where M is the theoretical mass value) based on the plots of the theoretical mass value and the relative error, and a procedure in which the observed mass value is calibrated by subtracting the systematic error from the entire measurement values.

For example, in the case of a time-of-flight mass spectrometer, the systematic error of a candidate molecule is determined from the aforementioned least square line. The systematic error is then subtracted from the entire actual measurement values. Specifically, the equation (Xc−M)/M=(X−M)/M−(aM+b), where X is an observed mass value, Xc is a calibrated mass value, and M is a theoretical mass value, is modified to Xc=X−M(aM+b).

Although the theoretical mass value M is given for the candidate molecule, it is not given to all of the actual measurement values. Therefore, if the entire actual measurement values are to be calibrated, the term M(aM+b) in the above equation must be approximated by an actual measurement value. The values of a and b are generally much smaller than those of X and Xc, such that M(aM+b)≈Xc(aX+b). Substituting this into the above equation yields Xc=X−Xc(aX+b), which can be modified to obtain Xc=X/(1+(aX+b)) based on which all of the observed mass values can be calibrated.

In accordance with the biopolymer automatic identifying method of the invention as described above, very accurate mass values can be obtained from complex biopolymer mixtures solely by data processing. The high accuracy of the resultant mass values makes it possible to identify and determine the biopolymers more unambiguously. Thus, the invention provides a highly reliable automatic identifying method capable of analyzing complex biopolymer mixtures.

The invention also provides information recording media, such as a CD-ROM, in which program information for causing a computer system to carry out the individual procedures constituting the above-described biopolymer automatic identifying method is stored.

The aforementioned means makes it possible to eliminate the calibration operation of the mass spectrometer prior to measurement and the addition of an internal standard to the sample in advance. It also allows the biopolymer automatic identifying method to be implemented with high accuracy and reliability based solely on data processing.

BEST MODE FOR CARRYING OUT THE INVENTION

Figure 1:
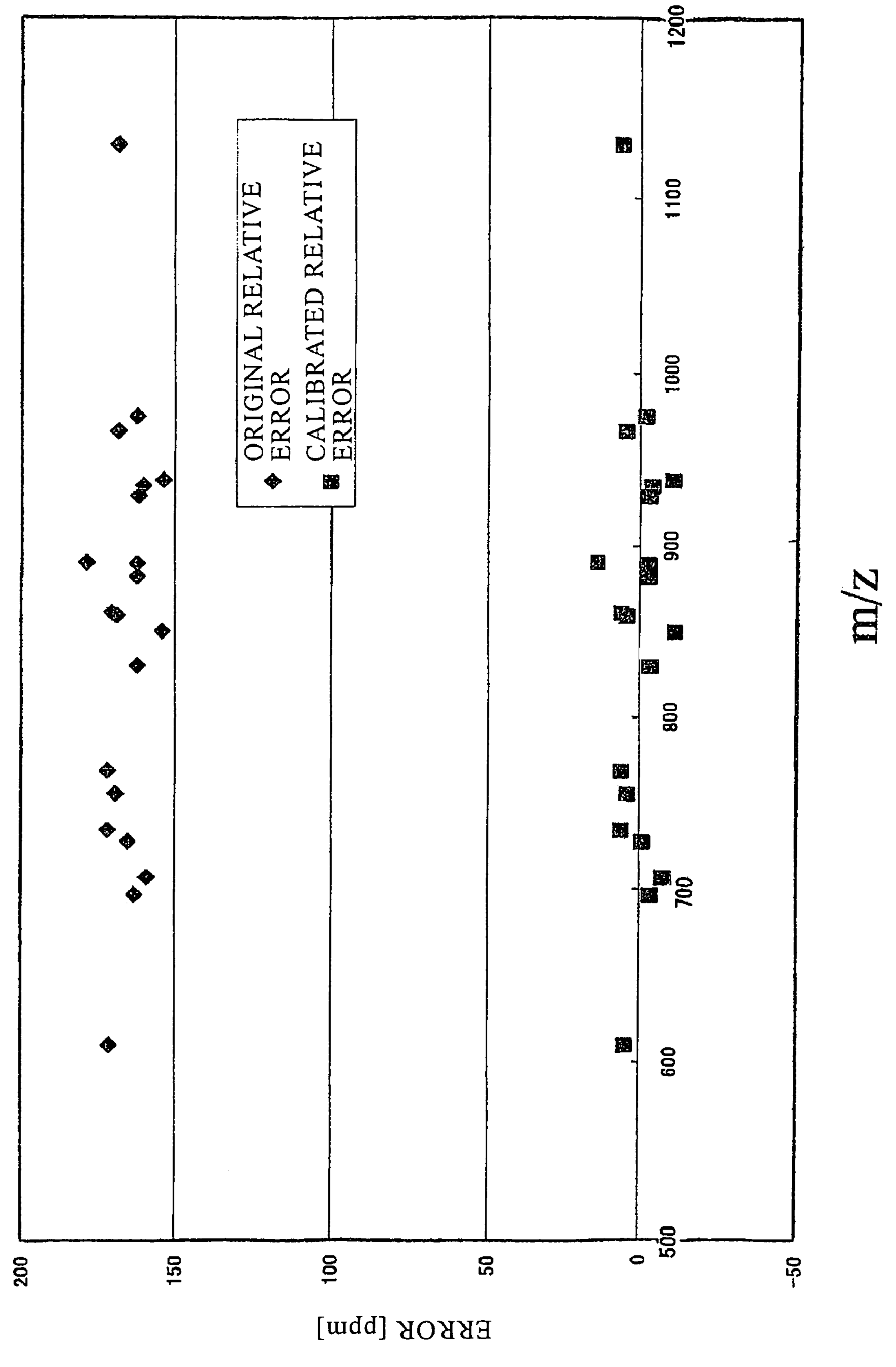
FIG. 1 shows the relationship between the mass value (m/z) identified in Example 1 and error.

A preferred embodiment of the biopolymer automatic identifying method in accordance with the invention will be described. It should be obvious, however, that the invention is not limited by the following embodiment.

The mass of an unknown biopolymer in a sample is initially measured by a conventional mass spectrometry method depending on purpose, thereby obtaining an observed mass value X. The mass spectrometry method may employ a tandem mass spectrometer, for example, which consists of a plurality of analyzers coupled in tandem. Specifically, in the tandem mass spectrometer, a particular ion (a parent ion) in a mixture is selected by the initial analyzer, and a collision dissociation is performed between the thus selected ion and an inert gas in the next analyzer. Then, a dissociated ion (generated ion) indicating the internal structure information is subjected to mass spectrometry by the final analyzer.

An observed mass value X obtained by the above mass measurement procedure is converted into a format (a binary file: mass value and intensity) that can be read by conventional database search engines. The thus converted value is then matched with a database in which a number of molecules with known mass values are stored, so as to search for a candidate molecule that could possibly be the unknown biopolymer under investigation.

For the conversion of the observed mass value X, any of the generally available types of software provided by the mass spectrometer manufacturers, such as MassLynx (from Micromass), may be appropriately utilized. The database search may be appropriately carried out by using any commercially available database software, such as Mascot (from Matrix Science).

From the results of the database search procedure, an arbitrary number of candidate molecules (or a set thereof) with high similarity scores are selected. The magnitude n of the set may be any number such that it renders statistical processing possible.

Thereafter, the relative error E between the observed mass value X and its theoretical mass value M of each of the candidate molecules selected by the above candidate molecule selection procedure is calculated in accordance with the following equation (1):

$$E=(X-M)/M \tag{1}$$

A mean value $m_E$ of the thus obtained relative error E is then calculated in accordance with the following equation (2):

$$m_E=\Sigma(E)/n \tag{2}$$

The standard deviation $S_E$ of the relative error E is then calculated by the following equation (3):

$$S_E=\{\Sigma(E-m_E)^2/(n-1)\}^{(1/2)} \tag{3}$$

Using this standard deviation, it is determined whether or not it is appropriate to use a particular candidate molecule for the internal standard. When $S_E<m_E$, the calibration is determined to be valid.

The magnitude of the systematic error is then estimated and subtracted from the observed mass value X, thereby obtaining a calibrated mass value Xc. For example, in the case of a time-of-flight mass spectrometer, the systematic error of the candidate molecule can be determined from the least square line y=ax+b with respect to the plots of the theoretical mass value and the relative error, in the following procedure. When the relative error after the calibration of the candidate molecule is Ec=(Xc−M)/M, Ec=E−(aM+b). Therefore:

$$(Xc-M)/M=(X-M)/M-(aM+b) \tag{4}$$

where X is an observed mass value, Xc is a calibrated mass value, and M is a theoretical mass value.

Specifically, the above equation (4) is modified to obtain the following equation (5):

$$Xc=X-M(aM+b) \tag{5}$$

It is noted that although the theoretical mass value is given for the candidate molecule, it is not given for all of the actual measurement values. Therefore, in order to calibrate all of the actual measurement values, the term "M(aM+b)" in the equation (5) must be approximated by an actual measurement value. The values of a and b are generally much smaller than those of X and Xc, such that M(aM+b)≈Xc(aX+b). Substituting this into Equation (6) yields the following equation (6):

$$Xc=X-Xc(aX+b) \quad (6)$$

This equation (6) is modified to obtain the following equation (7):

$$Xc=X/(1+(aX+b)) \quad (7)$$

based on which all of the observed mass values are calibrated.

The values of b and a in the aforementioned least square line can be determined from the following equations (8) and (9), respectively:

$$b=\Sigma\{(M-m_M)\times(E-m_E)\}/\Sigma\{(M-m_M)\hat{}2\} \quad (8)$$

$$a=m_E-b\times m_M \quad (9)$$

The value of $m_M$, which is the mean value of the theoretical mass value M of the candidate molecule, can be determined from the following equation (10):

$$m_M=\Sigma(M)/n \quad (10)$$

The relative error Ec between the mass value Xc after mass calibration and the theoretical mass value m can be determined from the following equation (11):

$$Ec=E-(aM+b) \quad (11)$$

Thereafter, the mean value $m_{Ec}$ of the relative error Ec=(Xc−M)/M obtained for the candidate molecule and the standard deviation $S_{Ec}$ are determined from the following equations (12) and (13), respectively:

$$m_{Ec}=\Sigma(Ec)/n \quad (12)$$

$$S_{Ec}=\{\Sigma(E-m_{Ec})^2/(n-1)\}^{(1/2)} \quad (13)$$

Based on the thus obtained mean value $m_{Ec}$, the calibration is evaluated. Ideally, $m_{Ec}=0$. Tolerance Tc for a database search is then calculated based on the standard deviation $S_{Ec}$, using the following equation (14):

$$Tc=K\times S_{Ec} \quad (14)$$

where K is 1.5 to 3.0, thereby completing the above-described series of calibration procedures.

In the above equation (14), K is an empirical constant for designating the confidence interval of the mass value. The K value can be appropriately determined depending on the accuracy of the software used for the database search. The higher the identification performance of the database search software, the closer K can be to 3, where a 99.7% confidence interval can be obtained. In the case of Mascot (Matrix Science) database software, K=1.5 can be empirically employed.

Based on the resultant tolerance Tc ($Tc_1$), the same database search is conducted once again. As needed, the above-described series of calibration and database search procedures are repeated a plurality of times so as to narrow the range of the tolerance Tc ($T\rightarrow Tc_1\rightarrow Tc_2\rightarrow \ldots$) gradually, thereby enhancing the candidate molecule selection accuracy. $Tc_1$ indicates the tolerance obtained by the initial calibration operation, and $Tc_2$ indicates the tolerance obtained by the second calibration operation.

In this way, the accuracy of candidate molecule identification can be enhanced. Namely, the accuracy of identification of unknown sample molecules can be improved.

The above-described procedures can be rendered into desired computer program information which can then be stored in various forms of information recording media, such as CD-ROMs, Floppy™ discs, or other forms of computer hardware, such as servers. In this way, the program can be executed on a desired computer system or a computer network (via information and communications technology).

EXAMPLES

The time-of-flight mass spectrometer is an apparatus for measuring the time it takes for an ion to travel a certain distance L in order to measure its mass according to the relationship between the mass m and the time of flight T expressed by the following equation (15):

$$T=L\cdot(2\ \mathrm{eV})\hat{}(-1/2)\cdot(\mathrm{m/z})\hat{}(1/2) \quad (15)$$

where e is the elementary charge and z is the charge number.

The mass measurement accuracy of this apparatus depends on L and the acceleration voltage V. L, which is an inherent value of the apparatus, may fluctuate due to temperature-caused expansions or contractions. V may fluctuate due to the drift in the supply voltage. Depending on the measurement conditions, these fluctuations may cause a systemic mass error of 100 ppm or more. However, variations among mass errors (which reflect the performance of the mass spectrometer) are relatively small as compared with the mean value of the systematic error. By taking advantage of this fact, the systematic error can be exclusively eliminated.

In the following, an example in which identification accuracy has been improved by the method of the invention will be described.

Example 1

One hundred fmol of tryptic digest of human serum albumin was measured by HPLC-MS/MS, and a database search was conducted by MS/MS ions search using the commercially available Mascot database search software (search parameters: peptide tolerance 250 ppm; and MS/MS tolerance 0.5 Da).

Based on the search results, the relative error E ((X−M)/M ppm) with respect to the theoretical m/z identified for the 20 ions with the highest scores was determined. The relative error E was then plotted with respect to the theoretical m/z, as shown in FIG. 1. As shown, the mean value of the original relative error E (indicated by ♦) was approximately 170 ppm, whereas the variations in E were within the 150-175 ppm range, which are smaller than the value of E per se.

The mass was calibrated by finding a least square line with respect to this group of ions and then subtracting it from the error in each ion. The relative error Ec after calibration (indicated by ■ in FIG. 1) was similarly plotted, as shown in FIG. 1. The database search parameters determined from the variations in Ec (represented by the standard deviation) were such that the peptide tolerance was 18 ppm and the MS/MS tolerance was 0.080 Da. Thus, the mass calibration allowed the tolerances in a search to be reduced from 250 to 18 ppm and from 0.5 to 0.080 Da; namely, by a factor of approximately 14 and 6, respectively, thereby enhancing the identification reliability.

Example 2

The following shows that erroneous identification can actually be corrected by the mass calibration method of the invention.

Figure 2:
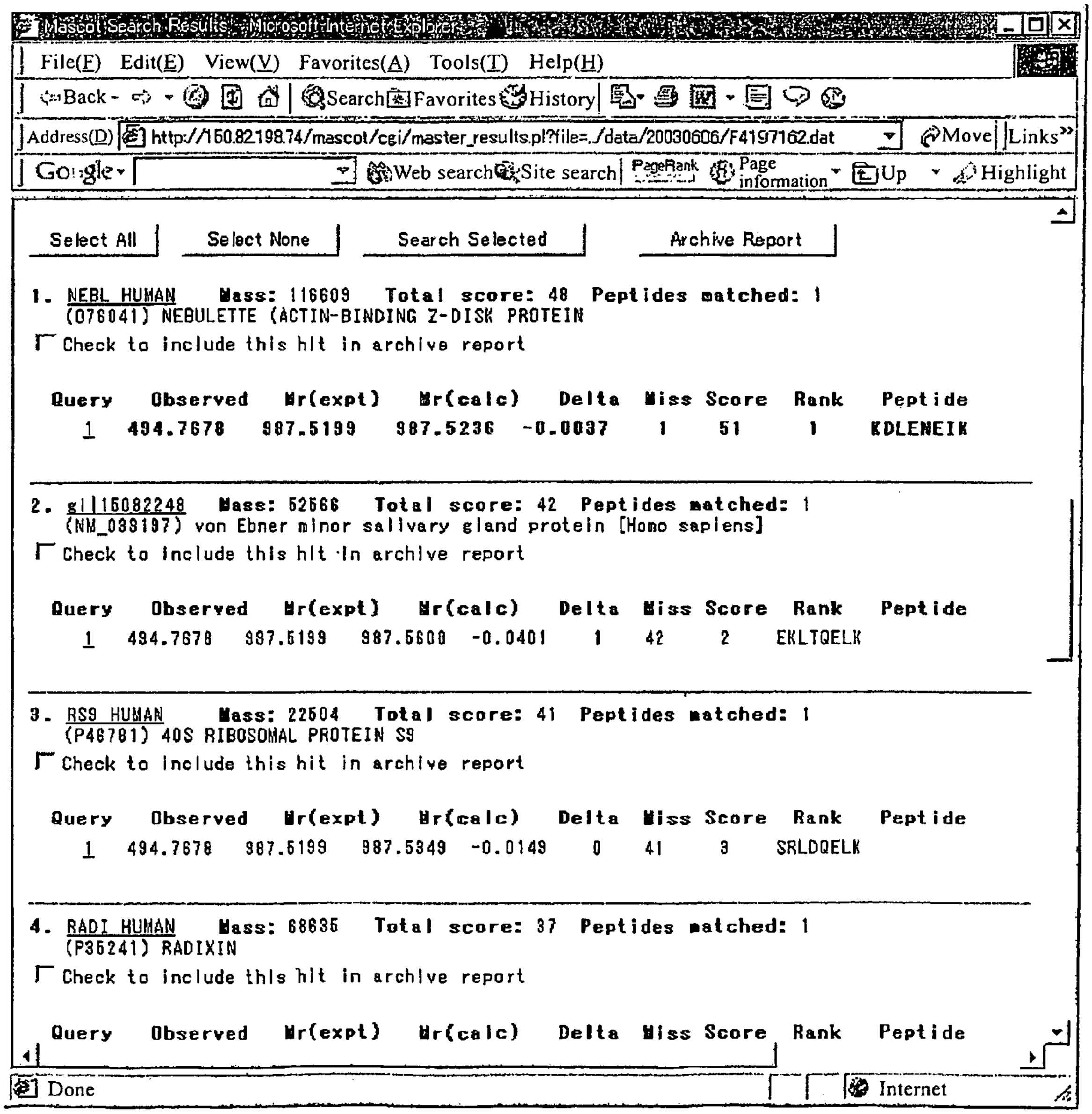
FIG. 2 shows the result of identification prior to mass calibration in Example 2.

A peptide SRLDQELK, which is known to be liable to erroneous identification during a database search based on mass data, was synthesized in a conventional manner. One hundred fmol of the peptide was then mixed with 100 fmol of the aforementioned tryptic digest of human serum albumin, and a similar experiment was conducted. Under the conventional search conditions (with search parameters of peptide tolerance 250 ppm and MS/MS tolerance 0.5 Da), the synthetic peptide was erroneously identified, as shown in FIG. 2.

Figure 3:
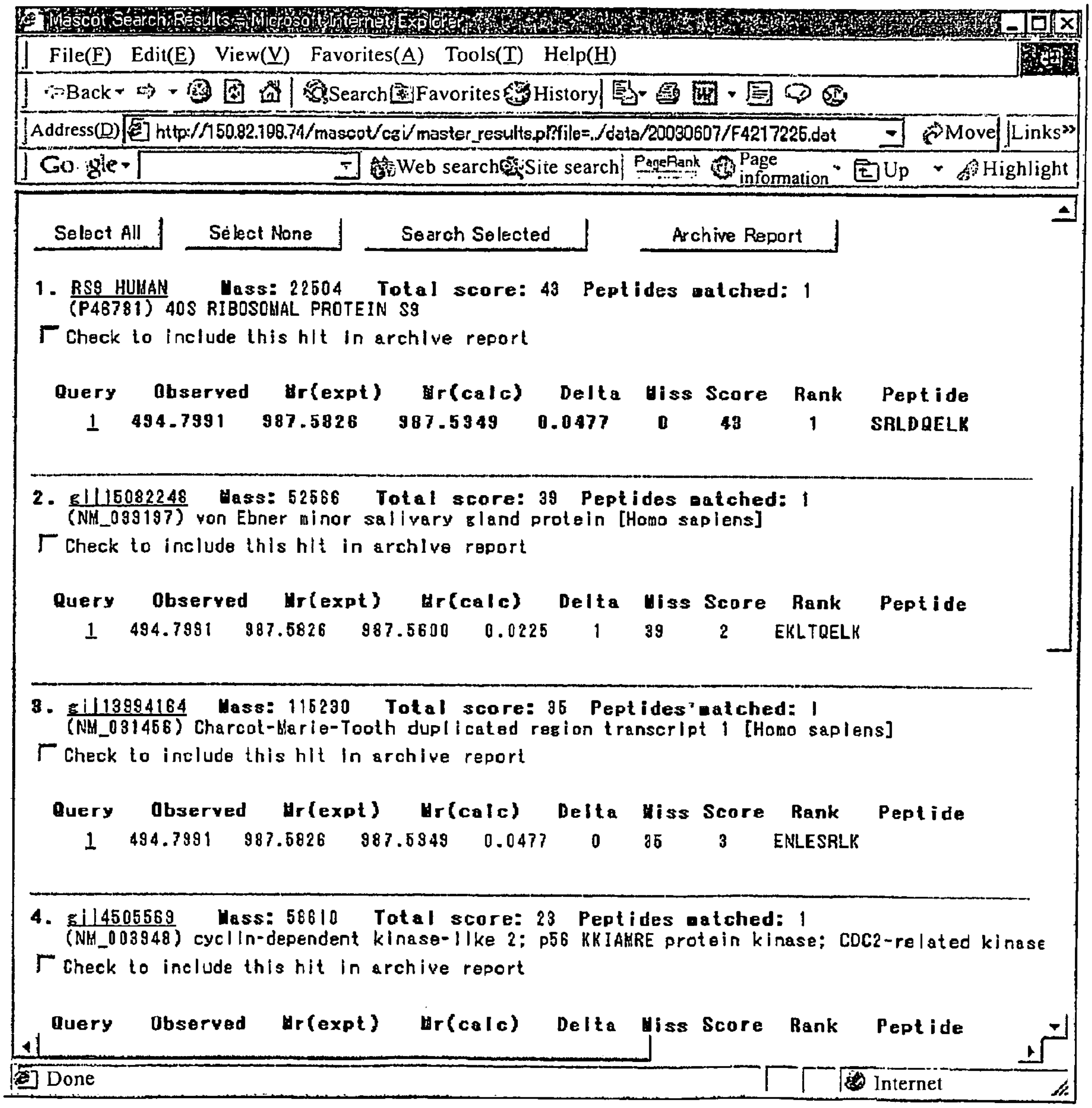
FIG. 3 shows the result of identification after mass calibration in Example 2.

When the above-described mass calibration was performed, the peptide was correctly identified, as shown in FIG. 3.

Figure 4:
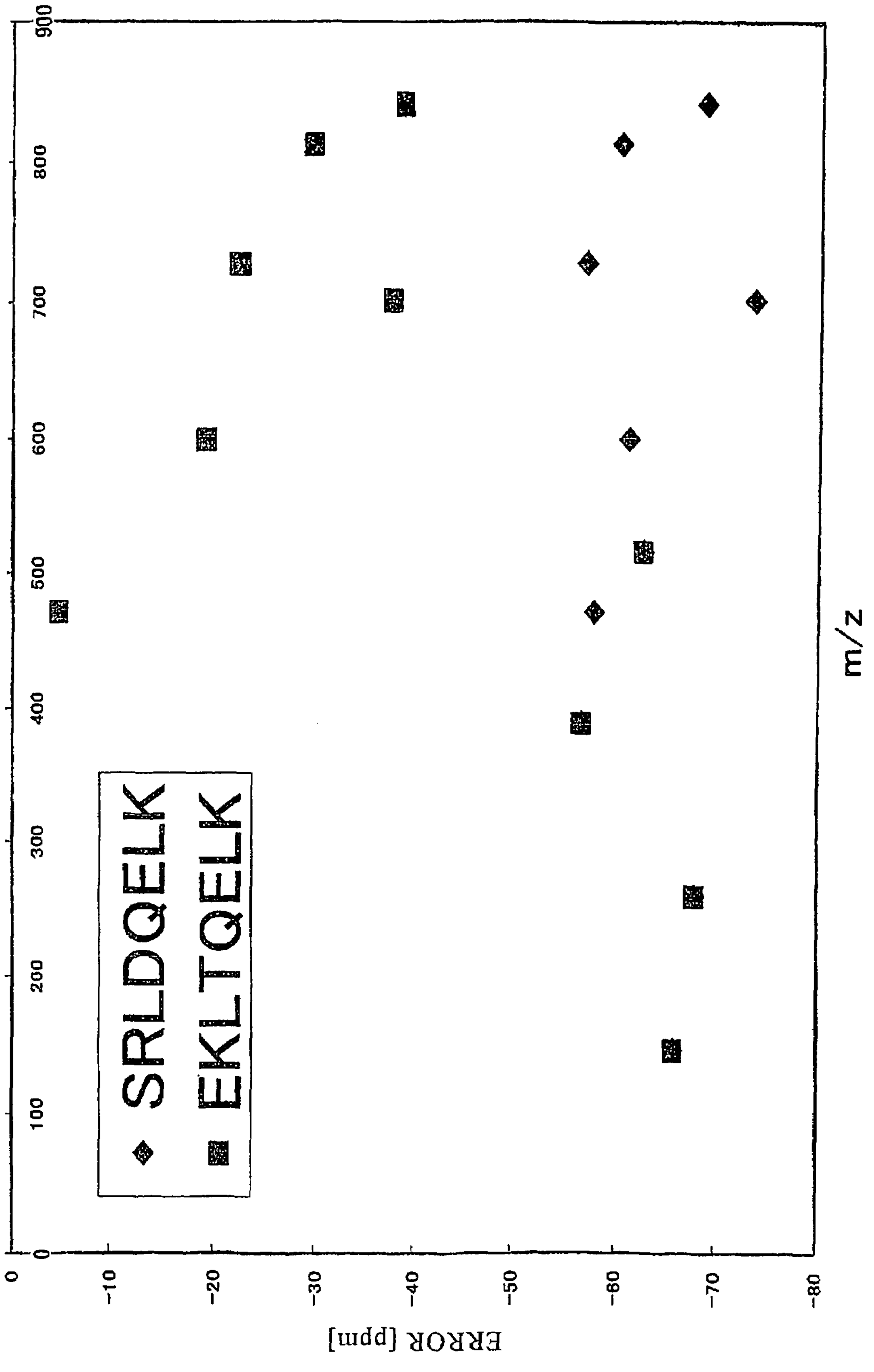
FIG. 4 shows the relationship between the mass value (m/z) identified in Example 2 and error.

Each ion in the MS/MS spectrum of the peptide was assigned to a theoretical product ion (b and y ion sequences) of each peptide (EKLTQELK and SRLDQELK) that had been identified, and its systematic error was plotted with respect to the m/z, as shown in FIG. 4. In the case of SRLDQELK (indicated by ♦ in FIG. 4), the relative error of all of the ions was within a narrow range, whereas in the case of EKLTQELK (indicated by ■ in FIG. 4), the plots exhibited two different distributions. Thus, by improving the mass accuracy by data processing, it became possible to correctly distinguish and identify peptides with similar masses and with identical sequences in the c-terminal portion.

INDUSTRIAL APPLICABILITY

In accordance with the invention, the calibration operation of the mass spectrometer prior to measurement, or the addition of an internal standard to a sample, can be eliminated, thereby enabling continuous operation of the mass spectrometer (without interruption by calibration operations). As a result, operators are freed from the burden of equipment adjustment, such that the efficiency of the molecule identification operation can be improved.

Furthermore, the influence of error inherent in a mass spectrometer can be eliminated, and a highly accurate and reliable biopolymer automatic identifying method can be implemented based solely on data processing. In a measurement system employing a plurality of mass spectrometers, uniform data accuracy can be obtained in individual mass spectrometers, thereby reliably preventing the erroneous identification of an unknown sample molecule.

The invention claimed is:

1. A biopolymer automatic identifying method, comprising:

(a) obtaining a plurality of observed mass values, by subjecting a sample comprised of one or more biopolymers to MS/MS, producing candidate molecules;

(b) matching at least one of said observed mass values with a theoretical mass value, in a predetermined database of known mass values using a suitably programmed computing device, for candidate molecules, wherein one of said candidate molecules has a high similarity score such that it is thereby identified as an internal reference; then (c) selecting at least one candidate molecule from (b) that has such a high similarity score using a suitably programmed computing device;

(d) calibrating said plurality of observed mass values with said internal reference to produce calibrated mass values using a suitably programmed computing device, wherein said internal reference is the theoretical mass of the selected candidate molecule or molecules in (c), and wherein each of said calibrated mass values is determined by the equation $$Xc=X/(1+(aX+b)),\text{ wherein}$$

Xc is a calibrated mass value,

X is an observed mass value, $$b=\Sigma\{(M-mM)\times(E-mE)\}/\Sigma\{(M-mM)2\},$$

$$a=mE-bXmM,$$

$$E=(X-M)/M,$$

$$mE=\Sigma(E)/n,\text{ and}$$

$$mM=\Sigma(M)/n,$$

wherein M is the theoretical mass value for said candidate molecule and n is the total number of candidate molecules;

(e) calculating relative error between said calibrated mass value of a candidate molecule in (d) and a theoretical mass value to determine the standard deviation of said relative error using a suitably programmed computing device;

(f) determining a tolerance of the matching step using said standard deviation (e) and a suitably programmed computing device, wherein said tolerance is determined by the equation $$T_c-K\times S_{EC},\text{ wherein K is 1.5 to 3.0; optionally,}$$

(g) repeating steps (b)-(f) using a suitably programmed computing device; and then (h) comparing said calibrated mass values to said predetermined database, thereby to determine the identity of at least one of said biopolymers using a suitably programmed computing device.

2. The biopolymer automatic identifying method according to claim 1, wherein said sample comprises more than one biopolymer.

3. The biopolymer automatic identifying method according to claim 1, wherein each mass value is matched with one candidate molecule.

4. The biopolymer automatic identifying method according to claim 1, further comprising communicating said identity to a display or to a computer storage medium.

5. The biopolymer automatic identifying method according to claim 1, wherein said calibrating step comprises: (A) calculating a relative error between said mass values and the theoretical mass in (d); (B) estimating a systemic error of said mass values by creating a least square line by plotting the theoretical mass in (d) against said relative error; and (C) subtracting said systemic error from said calibrated mass values, $X_c$.

6. An information recording medium in which program information for causing a computer system to carry out the individual procedures of biopolymer automatic identifying method according to claim 1 is stored.

* * * * *